(12) United States Patent
Suzuki et al.

(10) Patent No.: US 8,309,128 B2
(45) Date of Patent: Nov. 13, 2012

(54) STABILIZED MILNACIPRAN FORMULATION

(75) Inventors: Kazumi Suzuki, Tokyo (JP); Hitoshi Yamada, Tokyo (JP)

(73) Assignee: Pierre Fabre Medicament, Boulogne-Billancourt (FR)

( * ) Notice: Subject to any disclaimer, the term of this patent is extended or adjusted under 35 U.S.C. 154(b) by 437 days.

(21) Appl. No.: 11/921,888

(22) PCT Filed: Jun. 8, 2006

(86) PCT No.: PCT/JP2006/311495
§ 371 (c)(1),
(2), (4) Date: Jul. 16, 2008

(87) PCT Pub. No.: WO2006/132307
PCT Pub. Date: Dec. 14, 2006

(65) Prior Publication Data
US 2009/0049935 A1   Feb. 26, 2009

(30) Foreign Application Priority Data
Jun. 10, 2005  (JP) .................. 2005-171276

(51) Int. Cl.
*G01N 33/15* (2006.01)
*A61K 31/165* (2006.01)
*A61K 9/36* (2006.01)

(52) U.S. Cl. ..................... 424/479; 73/865.3

(58) Field of Classification Search .................. 424/479; 73/865.3
See application file for complete search history.

(56) References Cited

U.S. PATENT DOCUMENTS

| 4,478,836 A | 10/1984 | Mouzin et al. |
| 5,543,393 A | 8/1996 | Kim et al. |
| 7,097,793 B2 * | 8/2006 | Lin et al. .................. 264/42 |
| 2003/0108602 A1 * | 6/2003 | Chu et al. .................. 424/465 |
| 2003/0232805 A1 | 12/2003 | Kranzler et al. |
| 2004/0180091 A1 | 9/2004 | Lin |

FOREIGN PATENT DOCUMENTS

| JP | 58-4752 A | 1/1983 |
| JP | 8-141383 A | 6/1996 |
| JP | 9-501701 A | 2/1997 |
| JP | 10-287561 A | 10/1998 |
| JP | 2000-516946 A | 12/2000 |
| JP | 2003-277252 A | 10/2003 |
| JP | 2004-277422 A | 10/2004 |
| JP | 2005-104934 A | 4/2005 |
| WO | WO-00/38655 A1 | 7/2000 |
| WO | WO-2004/039361 A1 | 5/2004 |

* cited by examiner

*Primary Examiner* — San-Ming Hui
*Assistant Examiner* — Kathrien Cruz
(74) *Attorney, Agent, or Firm* — Birch, Stewart, Kolasch & Birch, LLP

(57) ABSTRACT

It is intended to provide a milnacipran formulation which is more stable than a conventionally known milnacipran formulation, and a method of stabilizing a milnacipran formulation. The object could be achieved by using a milnacipran-containing composition in which milnacipran or a salt thereof is allowed to exist in a porous carrier, packing a powder containing milnacipran or a salt thereof in an HPMC capsule, or combining an additive which does not cause an interaction with milnacipran with time.

8 Claims, No Drawings

STABILIZED MILNACIPRAN FORMULATION

TECHNICAL SPHERE

The present invention relates to a stabilized milnacipran formulation which has improved formulation deterioration characteristics.

BACKGROUND TECHNOLOGY

Milnacipran (chemical name: (±) cis-2-amino methyl-N, N-diethyl-1-phenyl cyclopropane carboxamide) is a new antidepressant called SNRI (Serotonine Noradrenaline Selective Reuptake Inhibitor) which has a very low affinity to receptors of various types of intracerebral neurotransmitters, while it was also indicated that its effect rivals the effect of tricyclic antidepressants represented by Imipramine because it blocks the reuptake of noradrenaline in addition to serotonine. Milnacipran is sold in Japan as a tablet which is provided with a film coating (trade name: TOLEDOMIN TABLET), while overseas it is sold as a capsule preparation (trade name: IXEL).

Milnacipran manufacturing methods have been described in the reports provided in Patent Bibliography 1 through 3 listed below. In addition, according to the report listed below in Non-Patent Bibliography 1, a toledomin tablet can be obtained as a tablet preparation which has a decreased hardness and which can be stored in environment characterized by high humidity, while Non-Patent Bibliography 4 and 5 are reports describing preparations containing milnacipran.

Patent Bibliography 1: Japanese Examined Patent Application Number 63-23186.
Patent Bibliography 2: Japanese Examined Patent Application Number 05-67136.
Patent Bibliography 3: Japanese Patent Number 2964041.
Patent Bibliography 4: Japanese Patent Publication Number 2000-516946.
Patent Bibliography 5: Japanese Patent Publication Number 2002-519370.
Non-Patent Bibliography 1: "Pharmavision" K. K. Company, June 2003, Volume 6, P. 24.

DISCLOSURE OF THE INVENTION

Problem to Be Solved by This Invention

The present invention provides a stabilized milnacipran formulation and a method to manufacture a stabilized milnacipran formulation from milnacipran formulations known from prior art.

Means to Solve Problems

The inventors of this invention discovered that new problems related to milnacipran formulations prepared according to prior art must be overcome because when various types of manufactured formulations which contain milnacipran are stored, discoloration of the formulation occurs during handling, and if milnacipran is stored in an environment which has a high humidity, problems such as adhesion of individual tablets to each other or adhesion to the packing container tend to occur.

For example, in the case of tablets which are provided with a film coating, adhesion of tablets is accompanied by peeling off of the film coating. At the same time, the tablet preparation is deformed and other forms of deterioration such as breaking and the like can easily occur, while solidification or coagulation can easily occur with granular preparations of preparations in the form of powder. When elution tests were performed of preparations having the form of a capsule, there is a risk that the drug effect will not be manifested when the drug is taken internal if elution of milnacipran from the capsule is greatly delayed. In particular when the tablet is stored in very humid locations, deformation and cracks of the tablets can easily occur, the tablets can easily become sticky, and they can stick to each other. In addition, when elution tests of sugar-coated tablets were performed, there was also a possibility that a different drug efficacy could be manifested when the tablets were ingested. Because toledomin tablets (film-coated tablets) were considered stable under conditions involving a high humidity level, the preparations used for these tablets were manufactured with conventional methods using anhydrous calcium hydrogen phosphate, which is an additive that has a low moisture absorption that is within the range that is pharmacologically acceptable for additives. However, since prevention of the deterioration of the formulation has not been achieved so far, a stable milnacipran is not obtained when the tablets are stored under conditions involving a high humidity level.

In order to resolve the problems mentioned above, the inventors of this invention have unexpectedly discovered as a result of intensive research that milnacipran that has been dissolved in a solvent can be adsorbed on a porous substance (carrier) during operations such as granulation and spray drying, even when an inorganic compound is used, such as anhydrous calcium hydrogen phosphate or the like (1) (i). When this type of a composition which contains dried milnacipran is used, it is possible to prevent viscous (sticky) characteristics and adhesion under conditions involving a high humidity even when a completely identical tablet preparation is used having the same formulation composition with a capsule formulation (ii). Since milnacipran adheres to a porous carrier when a carrier is used as the filler in a capsule formulation, the delayed elution does not take place. (2) Because this makes it possible to prevent deformation, breaking, and tackiness when the capsules are stored under conditions involving a high humidity, deformation, breaking and tackiness occurring during storage under conditions involving a high humidity can be prevented when a capsule made of hydroxyl propyl methyl cellulose (HPMC) is filled with a powder containing milnacipran. When a composition containing milnacipran is employed, wherein milnacipran adheres to a porous carrier used with a sugar coated tablet, uneven elution of each tablet can be prevented (3). Moreover (4), due to the effect of the interaction occurring after some time has elapsed between milnacipran and D-mannitol in compositions containing this and other additives, changes in the external appearance of a composition containing milnacipran and/or of the milnacipran formulation, such as discoloration, can be also prevented. This invention was thus perfected on the basis of these findings.

Specifically, the present invention relates to the following items.
(1) A composition containing milnacipran, which is manufactured using a milnacipran formulation wherein milnacipran or a salt thereof is allowed to exist in a porous carrier;
(2) The composition described in item (1), wherein the milnacipran or a salt thereof is milnacipran chloride;
(3) The composition described above in (1) and (2), having a porous carrier composition which is a porous carrier composition that is obtained from a pharmacologically acceptable inorganic substance;

(4) The composition described in any of the items (1)~(3) above, wherein the porous carrier composition is selected from anhydrous calcium hydrogen phosphate, calcium hydrogen phosphate, kaolin, hydrous silicon dioxide, calcium silicate, magnesium silicate, light anhydrous silicate, magnesium metasilicate aluminate, diatomaceous earth, synthetic aluminum silicate, dry aluminum hydroxide gel, magnesium carbonate, calcium carbonate, silicon dioxide, bentonite, calcium sulfate, activated carbon or mesoporous silica, wherein only one such item type can be used or two or more can be combined together.

(5) The composition described in any of the times (1)~(4) above, wherein the porous carrier composition can be selected from anhydrous calcium hydrogen phosphate, hydrous silicon dioxide, calcium silicate, magnesium silicate, light anhydrous silicate or magnesium metasilicate aluminic acid, wherein only one such item type can be used or two or more can be combined together;

(6) The composition described in items (1)~(5) above, wherein the porous carrier composition is a porous carrier which contains anhydrous calcium hydrogen phosphate;

(7) The composition described in items (1) and (2) above, wherein the porous carrier comprises a pharmacologically acceptable organic substance;

(8) The composition described in items (1), (2), or (7), wherein the porous carrier includes starches and granulated starches, cellulose derivatives, dextrin, lactose or lauryl methacrylate;

(9) The composition described in any of the items (1)~(8) above, wherein after milnacipran or a salt thereof has been added to a porous carrier, milnacipran or a salt thereof is allowed to exist in the dried porous carrier;

(10) A composition containing milnacipran, wherein after milnacipran or a salt thereof, a pharmacologically allowable additive agent and a pharmacologically acceptable binder have been granulated with the wet method, drying is performed to induce the presence of milnacipran or a salt thereof in the porous carrier and/or in the formed porous carrier;

(11) A stabilized milnacipran composition, characterized by the fact that it contains the milnacipran composition described in any of the items (1)~(10) above;

(12) A stabilized milnacipran formulation provided with improved tackiness, characterized by the fact that it contains the milnacipran composition described in any of the items (1)~(10) above;

(13) A milnacipran formulation, characterized by the fact that it contains the milnacipran composition described in any of the items (1)~(10) above; wherein more than 80% of milnacipran or a salt thereof contained per the total amount of said formulation is present in the composition containing milnacipran;

(14) The milnacipran formulation described in any of the items (11)~(13) above, wherein the milnacipran formulation is a sugar-coated tablet;

(15) The milnacipran formulation described in any of the items (1)~(10) above, wherein a capsule is filled with the milnacipran formulation;

(16) A milnacipran formulation, wherein the composition containing milnacipran described in any of the items (1)~(10) above is a milnacipran formulation loaded into a capsule made of hydroxy propyl methyl cellulose (HPMC);

(17) A method to manufacture milnacipran or a salt thereof, wherein a pharmacologically acceptable additive and a pharmacologically acceptable binder are granulated, a porous carrier is formed, and after a milnacipran solution has been added next, milnacipran or a salt thereof are allowed to exist in the porous carrier;

(18) A method for stabilization of a milnacipran formulation, wherein milnacipran or a salt thereof are allowed to exist in a porous carrier;

(19) A method for stabilization of the elution of a sugar-coated milnacipran tablet, characterized by the fact that milnacipran or a salt thereof are allowed to exist in a porous carrier;

(20) A method for prevention of peeling of a film from the tablet of a milnacipran formulation, characterized by the fact that in a tablet containing a film-coated milnacipran formulation, milnacipran or a salt thereof is allowed to exist in a porous carrier;

(21) A method to suppress increased adhesiveness of a milnacipran formulation tablet, characterized by the fact that milnacipran or a salt thereof is allowed to exist in a porous carrier;

(22) A method to suppress decreased fluidity of the powder of a milnacipran formulation in the powder mode, characterized by the fact that milnacipran or a salt thereof is allowed to exist in a porous carrier;

(23) A method to suppress the surface tackiness of a capsule containing a milnacipran formulation, characterized by the fact that a composition containing milnacipran which is loaded into a capsule is allowed to exist in a porous carrier containing milnacipran or a salt thereof;

(24) A method for stabilization of the milnacipran formulation described in items (18)~(23) described above, characterized by the fact that the milnacipran or a salt thereof is milnacipran hydrochloride;

(25) The use of a porous carrier in order to increase the stability of a milnacipran formulation which contains milnacipran or a salt thereof.

(26) The use of a porous carrier described in item (25) above, wherein the milnacipran or a salt thereof is milnacipran hydrochloride;

(27) Milnacipran formulation, characterized by the fact that an HPMC capsule is filled with a powder which was prepared by mixing milnacipran or a pharmacologically acceptable salt thereof with a carrier;

(28) A method to test elution of a sugar-coated tablet of milnacipran described in item (14) above, characterized by the fact that retention of the sugar-coated milnacipran tablet at the bottom of the vessel is not allowed during the stirring based on Elution Testing Method No. 2 according the Japanese pharmacopoeia;

(29) The elution testing method for testing of the elution of a sugar-coated table containing milnacipran described in item (28) above, wherein a vessel having a convex part is used in the center at the bottom of the vessel;

(30) The elution testing method for testing of the elution of a sugar-coated tablet containing milnacipran described in item (28) above, characterized by the fact that a container is used in which a stationary disk is deployed in the center at the bottom of the vessel;

(31) The method for testing of the elution of a sugar-coated tablet containing milnacipran described in items (28)~(30) above, wherein 75 rpm is used for the number of revolutions;

(32) A composition containing milnacipran, wherein milnacipran or a salt thereof can be selected from a group of substances including D-mannitol, cornstarch, partially pregelatinized starch, sodium carboxymethyl starch, lower-substituted hydroxy propyl cellulose, carmelose, and calcium hydrogen phosphate, wherein at least one or more such substances can be selected.

Effect of the Invention

The present invention provides a milnacipran formulation which makes it possible to prevent tackiness, as well as adhesion, deformation, discoloration, breaking, consolidation, coagulation and the like when stored under conditions involving high humidity. Moreover, a milnacipran formulation can be provided which is stable with respect to elution.

PREFERRED EMBODIMENT MODES OF THE INVENTION

1. Milnacipran Formulation Containing a Formulation in which Milnacipran or a Salt Thereof is Allowed to Exist in a Porous Carrier The milnacipran according to this invention is known as F2207, TN-912, also known as dalcipran, midalcipran, or midalipran and its chemical formula is (±) cis-2-aminoethyl-N,N-diethyl-1-phenyl cyclopropane carboxamide. Milnacipran can be synthesized according to a known method (see Merck Index, $12^{th}$ Edition, Entry 6281).

In addition, while the milnacipran salt is not particularly limited as long as it is a salt of an acidic substance forming a milnacipran salt, it is desirable when this salt is a pharmacologically acceptable salt. Pharmacologically acceptable salts, which are again not particularly limited as long as these are salts forming a pharmacologically acceptable salt, example include for example hydrochloride, hydrobromide, nitrate, sulfate, phosphate, citrate, lactate, succinate, citrate, maleate, tartrate, fumarate, methane sulfate, p-toluene sulfate, as well as camphor sulfate or mandelate and other examples can be named. Among these salts, hydrochloride is preferred. This hydrochloride is also sometime called milnacipran hydrochloric acid or milnacipran hydrochloride.

According to this invention, a porous carrier is provided with fine apertures on the surface and in the inner part of the carrier on the specific surface area. However, there are no particular limitations as long as the surface or the inner part of the carrier is able to support this substance.

The porous carrier in which milnacipran or a salt thereof is allowed to exist is not particularly limited. The actual component forming the porous carrier can be a porous substance (a pharmacologically allowable additive), or components which form a porous substance upon coagulation can be also used as a porous carrier.

It is desirable when the component forming a porous carrier is a pharmacologically allowable component (a pharmacologically allowable additive); for example an anhydrous calcium hydrogen phosphate can be used for a inorganic compound, or calcium hydrogen phosphate, kaolin, hydrous silicon dioxide, calcium silicate, magnesium silicate, light anhydrous silicate, magnesium metasilicate aluminate, diatomaceous earth, synthetic aluminum silicate, dry aluminum hydroxide gel, magnesium carbonate, calcium carbonate, silicon dioxide, bentonite, calcium sulfate, activated carbon or mesoporous silica and other examples can be listed. Anhydrous calcium hydrogen phosphate, calcium hydrogen phosphate, hydrous silicon dioxide, calcium silicate, magnesium silicate, light anhydrous silicate, or magnesium metasilicate aluminate are particularly preferred, in particular anhydrous calcium hydrogen phosphate, or calcium hydrogen phosphate, while anhydrous calcium hydrogen phosphate is particularly preferred.

In addition, the components used in order to form a porous carrier can be selected so as to minimize the amount of dissolved substance generated when a milnacipran-containing substance is stored under specified conditions, since it is preferable when a porous substance is selected which has the smallest amount of dissolved substance. For example, the term customary conditions used for storage means 25° C. during the storage period of 36 months with a relative humidity of 60% to give an example of a customary storage method. Moreover, 40° C. with a shorter storage period, or a relative humidity of 75% with a storage period of 6 months are also possible examples, as is 60° C. during a storage period of 2 weeks and other examples can be provided.

While the method used to measure the amount of dissolved substance is not particularly limited, the liquid chromatography method is commonly used for this purpose with a detector using an ultraviolet ray spectrometer and other examples can be indicated. Stability tests used to test the storage conditions described above according to the storage method are based on "Guidelines for Impurities in Formulations Used in Pharmaceutical Products Containing New Effective Ingredients issued by the International Conference on Harmonization (ICH). Since stable characteristics are confirmed when the amount of the dissolved substance determined with this method is below 0.05%, it is desirable when the amount of the dissolved substance generated during the storage period under specified conditions is less than 5%.

When anhydrous calcium hydrogen phosphate is used for the porous carrier of the milnacipran formulation of this invention, less than 0.1% of generated dissolved substance is indicated with storage at 60° C. during a period of 2 weeks.

For the components which form an organic porous carrier (as a pharmacologically acceptable additive) can be used starches or granulated starches, crystalline cellulose or granulated crystalline cellulose, cellulose derivatives, dextrin, lactose or lauryl methacrylate and other examples can be mentioned.

A preferred example of components which form an organic porous carrier (as a pharmacologically acceptable additive) is anhydrous calcium hydrogen phosphate, among other indicated examples. It is desirable when spray-drying of anhydrous calcium hydrogen phosphate is used to manufacture a porous substance.

According to this invention, the method used to allow the presence of milnacipran in a porous carrier is not particularly limited, as long as a stabilized composition can be obtained which contains milnacipran. For example, a method using direct adsorption in a porous substance can be employed, or the spray adsorption method which will be described later, or the mixed adsorption method, or the spray-drying method and other examples can be named. In addition, the wet granulation method can be used for adsorption while a porous carrier is formed and other examples can be mentioned.

Moreover, the term "stabilized" as used in this invention relates to the state of tackiness, discoloration (change of external appearance), and to the extent of reduced coagulation and similar examples can named. In addition, the term "stabilized" also includes a state wherein irregular elution of milnacipran from the formulation is limited.

The milnacipran-containing formulation of this invention can be manufactured with a customary method, for example so that milnacipran is dissolved in a solvent and adsorbed in a porous carrier and a formulation containing milnacipran is obtained after drying.

An adjustment of the milnacipran solution is required during the adsorption of milnacipran in a porous carrier. However, since it is desirable when the solvent used to dissolve milnacipran is a substance having a low toxicity, a pharmacologically acceptable solvent is preferred. A solvent that is suitable for this purpose is for example water, ethanol, methanol, acetone and the like. Moreover, it is also preferred when two or more such solvents are mixed together. The amount of the solvent to be used for dissolution is not particularly limited as long as the milnacipran is dissolved. It is thus possible to use for example 0.5 parts by weight per 1 part by weight of milnacipran for the lower limit of this amount, while at least 1.0 parts by weight is preferred, and no more than 2.0 parts by weight is even more preferred.

Also, while the upper limit for this amount will depend on the time required for the manufacturing, since a long time period will be required for a very large solvent amount, less than 5 parts by weight is usually preferred, while less than 3 parts by weight is even more preferred.

The compounding amount of the porous carrier can be selected with a suitable amount inducing adsorption of milnacipran in the porous carrier. While the amount of milnacipran contained in the formulation as the effective ingredient can be modified according to the applicable symptoms and conditions of the patient, it usually ranges from 10~100 mg. The amount in a porous carrier inducing adsorption of milnacipran is indicated in one example as 25~250 mg. A more desirable amount of milnacipran contained in the formulation is 15~25 mg. A desirable amount of a porous carrier inducing adsorption of this amount of milnacipran is 40~80 mg. It is possible to use only one type of a porous carrier inducing adsorption of milnacipran contained in the formulation, or several porous carrier types can be also used.

While the method to be used in order to induce direct adsorption of milnacipran in a porous carrier is not particularly limited, it is possible to use a method wherein i) after adsorption of milnacipran solution has been achieved by spraying the solution on a pharmaceutically acceptable carrier or when spray-absorption of an emulsion liquid is used, drying is conducted (the spray adsorption method), ii) after milnacipran solution has been added to a porous carrier and adsorption has been induced by performing mixing with a mixer, drying is conducted (a method using mixing and adsorption), or iii) a porous carrier is added to a milnacipran solution so that an emulsion liquid is sprayed and dried (according to the spray-drying adsorption method) and other examples can be named.

According to a concrete example of the spray-adsorption method, a porous carrier is placed into a fluidized bed granulator (ST-1, made by the Powrex Company), so that while fluidization is induced in the floating state of the porous carrier by blowing wind into the granulator from the bottom part of the fluidized bed granulator, a milnacipran solution is sprayed from a spray nozzle and adsorption is induced with a method wherein drying is performed immediately thereafter inside the fluidized bed granulator and other examples can be mentioned. While the temperature of the air supplied during spray-adsorption of the milnacipran solution is not particularly limited when a porous carrier is fluidized, it is usually in the range of 20~60° C., although the range of 30~50° C. is preferred. In addition, although the temperature during drying is not particularly limited as long as decomposition of milnacipran does not occur, the range of 70~80° C. is normally used.

A concrete example of the mixing adsorption method is a method wherein a solution containing milnacipran is added to a porous carrier, mixing is performed with a mixer which is commonly used for manufacturing of formulations such as a V mixer or a rocking mixer or the like and after that, drying is performed in a fluidized bed granulator, etc.

After mixing and adsorption, the porous carrier containing adsorbed milnacipran must be dried. This drying can be performed by creating a floating state while air is blown into a fluidized bed granulator with a drying method using fluidization, or a drying method wherein air is blown into a rack drier can be used among other examples.

While the drying temperature is not particularly limited as long as this temperature does not cause decomposition of milnacipran, the range of 70~80° is usually employed.

According to the spray-drying adsorption method, for example a spray-dryer (type OCA-8: made by Ogawahara Koki Company) can be used to perform spray drying and other examples can be named.

To provide a more detailed explanation, according to a concrete example of the spray-drying method, milnacipran is dissolved in water, a porous carrier is added to this aqueous solution, the mixture is stirred and the created slurry status is dried for example with a spray drier (type OCA-8, made by the Ogawahara Koki Company) and sprayed at a high temperature in atmospheric air so that dried milnacipran is adsorbed by a porous carrier which is obtained in the powder form. Although the temperature during the spraying operation is not particularly limited as long as it is a temperature that does not cause decomposition and the like of milnacipran, the usually range is 100~200° C., while 150~180° C. is preferred.

It is also possible to allow milnacipran to be present in the porous carrier while the porous carrier is being formed. An example of this method is the wet granulation method among other examples. The wet granulation method is not particularly limiting with respect to the present invention as it is also possible to use for example the stirring granulation method or the fluidized granulation method or the like.

According to the stirring granulation method, a suitable additive that is pharmacologically acceptable, namely including components forming a porous carrier as described above and a suitable pharmacologically acceptable binder, for example pregelatinized starch, purulan, hydroxyl propyl methyl cellulose gum Arabic or the like, are added to the solution and mixing and granulation is performed so that a porous carrier is formed first, a milnacipran solution is added, and stirring is then followed by drying according to this method. In this case, it is necessary to provide two types of manufacturing equipment, namely a stirrer granulator which is used during the granulation stage, and a fluidized bed granulator which is used during the drying stage.

Also, according to the fluidized bed granulation method, a fluidized bed granulator is used so that a porous carrier is formed from the components which form the porous carrier. At the same time, while the porous carrier is fluidized in a current of air, a solution containing milnacipran is sprayed onto the carrier and the solution is adsorbed as is, which is followed by drying according to this method. This method makes it possible to simplify the manufacturing stages and to lower the manufacturing cost because it can be realized with one type of manufacturing equipment from adsorption to drying.

The status of the granulate can be confirmed with direct observation using an electronic microscope or the like, or a measurement of the specific surface area of the granulated substance can be used to ascertain whether a porous carrier was formed by removing the granulated substance and measuring it according to the gas adsorption method or the mercury gauge method or the like.

The milnacipran-containing composition obtained in this invention can be used directly as the milnacipran-containing preparation of this invention once a pharmacologically allowable carrier has been added to it. This milnacipran preparation is a stablet preparation in which tackiness or adhesion, deformation, breaking, consolidation, or agglutination or similar types of deterioration are prevented. The mode of the preparation is not particularly limited. It is thus possible to use for example a granular preparation, a powder preparation, a film-coated tablet, a capsule, a sugar-coated tablet, etc. Although no particular restrictions are specified as long as the formulation is stabilized, it is desirable when the content of milnacipran or a salt thereof which is present per the entire preparation amount is more than 80%, while the presence of more than 85% is preferred, the presence of more than 90% even more preferred, the presence of 95% still more preferred, and the presence of more 99% is optimal.

In the case of a tablet preparation which contains milnacipran of this invention, the tablet containing milnacipran can be formed by punching with a customary method used for manufacturing of tablets, wherein a suitable granular tablet is punched out directly after the adsorption powder containing milnacipran has been homogeneously mixed with a pharmacologically acceptable carrier.

A desirable size of the tablet is a size that does not cause problems during ingestion. In this case, the weight of 1 tablet is usually in the range of 50~300 mg, while 100~200 mg is preferred. In addition, the size of the tablet preparation is usually defined by a diameter in the range of 5 mm~10 mm, preferably 6 mm~8 mm.

A tablet obtained in this manner can be also coated with a coating film which is made of a suitable coating base material, so that a tablet provided with a film coating can be obtained, or a sugar-coated film can be also obtained which is coated with sugar.

For the method to be used for film coating can be used for example a method developed for pharmaceutical products published by the Hirokawa Publishing House, Volume 12, Formulation Ingredients, Chapter 2, paragraph 2.1.5. A preferable example of a suitable method is described in the chapter relating to coating preparations wherein a coating base material is dissolved in a liquid, a tablet formulation containing milnacipran is obtained with spraying or the like, which is followed by drying. The devices used to perform these operations can include a spray gun, a pan and an air blower, or a similar film coating device can be used such as a Doria coater (made by the Powrex Company) and other examples can be named.

It is also possible to add other substances to the base material of the coating which is used in the film depending on the purpose and other properties of the used material. For example, it is possible to select a suitable thermoplastic agent, a powder preparation, a coloring agent or a similar pharmacologically acceptable substance, and the coating base material described above can be also combined with the film coating. A suitable coating amount per the weight of the raw tablet containing milnacipran is 1~20% of the coating base material per the total weight of the raw tablet, while the range of 2~10% is preferred.

The method to be utilized to perform sugar coating of the tablet can use gelatin, gum Arabica, hydroxyl propyl methyl cellulose, hydroxyl propyl cellulose, sodium carmelose, polyethylene glycol, polyvinyl alcohol, purulan, or tragant or a similar binding agent, precipitated calcium carbonate, talc, titanium oxide, crystalline cellulose, calcium lactate, calcium sulfate, or a syrup solution having a solid content such as bentonite can be also used so that it is added dropwise to the tablet formulation containing milnacipran, an edge is created on the extended tablet and after a round shape has been formed, sucrose, D-mannitol, erythrytol, or maltitol or a similar syrup is added dropwise with a series of operations designed to created a smooth surface of an extended tablet among other examples of such methods.

A desirable amount to be used for sugar-coating per the weight of the raw tablet containing milnacipran is in the range of 10~150% per the total weight of the raw tablet, preferably in the range of 20~100%. In addition, a suitable range for the thickness of the sugar-coated layer is 0.1~1.5 mm, while the range of 0.4~1.0 mm is preferred, without being particularly limiting.

Desirable devices to be used with the sugar coating equipment performing sugar coating are a pan and an air blower. In addition, a Doria coater (made by the Powrex Company) can be also used to prepare the film coating.

The sugar-coated tablet which has been prepared in this manner can be simply mixed in a homogenous manner with milnacipran and a pharmaceutically acceptable carrier to prepare a sugar-coated tablet which can be used for comparison during an elution test so that individual fluctuations of the elution from the tablet can be decreased. When there are fluctuations of elution, they are attributable to irregular speed of elution.

In this invention, the wording "a capsule" is not particularly limited indicates examples such as examples of gelatin capsules or of HPMC capsules. A capsule preparation can be obtained when homogeneous mixing is applied to a porous substrate for milnacipran containing a pharmacologically acceptable carrier so that the mixture is loaded into a capsule. It is desirable when a capsule has a size that does not hinder ingestion when the capsule preparation is ingested. In this case, the amount of the powder which is loaded into 1 capsule is usually in the range of 50~300 mg, preferably 100~200 mg. In addition, a desirable size of a hard capsule is in the range of No. 1~No. 5, preferably No. 2~No. 4.

During an elution test of a capsule which has been manufactured in this manner, since a faster elution is indicated when milnacipran is that is homogeneously mixed with a porous carrier being a powder substance that is not pharmacologically acceptable when compared to a capsule obtained by filling a gelatin capsule or a HPMC capsule or a similar hard capsule, it is desirable when a porous carrier using an adsorption powder is used for milnacipran. Further, when a capsule is filled with a mixed powder which contains porous carrier adsorption powder with milnacipran, a stabilized milnacipran preparation can be obtained with a reduced adhesiveness even when the capsule is stored under conditions of high humidity. While no particular limitations are imposed with respect to the capsule, a better stability can be obtained with a gelatin capsule or with an HPMC capsule or a similar indicated example thanks to the stability of a capsule made of gelatin or HPMC, while an HPMC capsule is particularly preferred.

According to this invention, because milnacipran or a salt thereof is allowed to exist in a porous carrier with the method described above, a method is provided for the stabilization of a milnacipran preparation. Specifically, the method makes it possible to prevent and/or improve the characteristics of the milnacipran preparation containing milnacipran which is present in a porous carrier including tackiness, adhesion of individual preparation items, as well as adhesion to the packing container. When the milnacipran preparation is a tablet that is coated with a film, the damage or cracks, which is caused by the peeling of the film of said tablet, can be suppressed, etc., which makes it possible to prevent deterioration of the milnacipran preparation and/or create a stabilized design. According to this invention, a milnacipran preparation is provided with has improved tackiness and adhesiveness. It is particularly desirable when a milnacipran preparation is prepared which has improved tackiness.

The milnacipran preparation of this invention can be safely stored under conditions of high humidity. For example, the milnacipran preparation of this invention can be stored safely and without occurrences of deterioration of the preparation such as tackiness or the like even if the preparation is stored for a period of 1 day under relative humidity of 92%, and it can be stored safely and without occurrences of deterioration of the preparation such as tackiness or the like even if the preparation is stored for a 1 week period under relative humidity of 86%. Moreover, consolidation, coagulation or reduced fluidity can be suppressed when the milnacipran preparation is provided in the form of granules, or as a powder preparation or a powder, and it is also possible to suppress tackiness on the surface of the capsule when a capsule formulation is provided. While the capsule form does not impose particular limitations, it is desirable when for example a gelatin capsule or a HPMC capsule is used, although an HPMC capsule is preferred.

The use of the porous carrier within the scope of this invention also increases the stability of a preparation containing milnacipran or a salt thereof. It is also desirable when the porous carrier is formed from the components for the formation of a porous carrier mentioned above.

Fluidity is a characteristic which serves as a criterion of the deterioration of a preparation containing milnacipran such as a granular preparation or powder preparation. The angle of repose of a granular preparation or of a powder preparation can be measured in order to evaluate the stability of the preparation. For example, when the repose angle is measured before and after a granular preparation or a powder preparation has been stored at a high humidity, a greater repose angle before storage means that the fluidity characteristics have deteriorated. A granular preparation or a powder preparation which has a large repose angle makes it difficult to remove the preparation from a container and it is an obstacle to the ingestion of the preparation. While not being particularly limiting with respect to this repose angle, the repose angle can be measured with a device for measuring repose angle which is based on the cylindrical rotation method with three wheels.

Adhesiveness and/or tackiness also serve as a criterion of the deterioration of a preparation such as a tablet preparation and/or a capsule preparation containing milnacipran. Because this adhesiveness and/or tackiness causes a gradual tilting of a tablet placed on a smooth glass substrate which is free of irregularities, the angle by which a tablet preparation and/or a capsule preparation has slid and fallen can be measured to perform an evaluation. For example, by measuring the angle by which a tablet preparation and/or a capsule preparation has slid and fallen before and after this tablet preparation and/or a capsule preparation has been stored at a high humidity level, the deterioration of adhesiveness is indicated by a greater angle. A tablet preparation and/or a capsule preparation which has increased adhesiveness and/or tackiness can sometime adhere to the container or to a bag which is used for medication, which renders removal of the preparation difficult and which in turn can cause damage to the tablet preparation and/or capsule preparation.

2. Milnacipran Preparation Loaded into a HPMC Capsule

Further, the present invention also provides a milnacipran preparation containing a composition obtained in an HPMC capsule when milnacipran or a salt thereof is mixed with a pharmacologically acceptable carrier.

The wording "a composition which can be prepared with homogenous mixing of milnacipran or a salt thereof with a pharmacologically acceptable carrier" refers to a composition wherein milnacipran can be allowed to exist in a porous carrier as described above in 1., or it can also mean a composition wherein milnacipran or a salt thereof is not contained in a porous carrier and, as no particular limitations are imposed on the loaded composition containing milnacipran which is loaded into a HPMC capsule, although it is desirable when milnacipran or a salt thereof is present in a porous carrier. In addition, it is also desirable when the milnacipran preparation is loaded separately into such an HPMC capsule as this improves stability under conditions of high humidity; specifically, it improves the tackiness and adhesiveness on the surface of the capsule.

The devices which can be used for homogenous mixing of milnacipran or a salt thereof with a pharmacologically acceptable carrier are not particularly limited. It is thus possible to use for this purpose for example a V mixer or a rocking mixer and other example can be named. Moreover, as mentioned above, a suitable granulator can be used to manufacture a customary preparation in order to prepare a homogeneously mixed substance which can be loaded into a HPMC capsule. The powder containing milnacipran which has been charged into a HPMC capsule is not limited to a powder that is allowed to exist in a porous carrier, as it can also be a powder that is prepared by mixing in a homogenous manner milnacipran or a salt thereof with a pharmacologically acceptable carrier.

Adhesiveness and/or tackiness are used as a criterion of the deterioration of a preparation having the form of a capsule preparation which contains milnacipran. Because this adhesiveness and/or tackiness causes a gradual tilting of a capsule when it is placed on a smooth glass substrate which is free of irregularities, the angle by which a capsule preparation has slid and fallen can be measured to perform an evaluation. For example, by measuring the angle by which a capsule preparation has slid and fallen before and after this capsule preparation has been stored at a high humidity level, the deterioration of adhesiveness is indicated by a greater angle. A capsule preparation which has increased adhesiveness and/or tackiness can sometime adhere to the container or to a bag which is used for medication rendering removal of the preparation difficult, which in turn can cause damage to the capsule preparation and/or capsule preparation.

Elution test method for testing of stabilized elution of a sugar-coated tablet of milnacipran containing a composition in which milnacipran or a salt thereof is allowed to exist in a porous carrier.

According to this invention, a sugar-coated milnacipran tablet containing a composition in which the milnacipran or a salt thereof described above in 1. is allowed to exist in a porous carrier has a stabilized elution, without exhibiting fluctuations in the speed of elution. The present invention also provides a method for testing the elution of a sugar-coated milnacipran tablet.

When an elution test relating to a sugar-coated tablet is applied to a milnacipran preparation, the elution of milnacipran from the tablet preparation is greatly slowed down in the case of a fall directly under a rotary paddle shaft. In addition, a small deviation of the fall position exerts an influence which causes fluctuations of elution in individual tablets. The purpose of an elution test is to perform an evaluation as to whether the product quality of a solid preparation for internal ingestion is maintained at the same level. Even a small deviation of the fall position must be prevented as it exerts an influence on the test result. An elution test of a preparation which contains milnacipran is customarily performed according to the general method described in Elution Testing Method No. 2 of Japanese Pharmacopoeia (paddle method), so that water is used as the test solution and while the water temperature is maintained at 37° C., the test is performed with the paddle rotational speed of 50 rpm. In the case of this customary paddle method, the flow velocity f the test solution is slowed down in the vicinity of the front end of the stirring wheel of the paddle, and since the closer to the rotary axle, the slower the flow velocity becomes, it is thought that the slowest flow velocity is obtained directly below the rotary axle. When an elution test is conducted, the flow velocity of the test solution, that is to say the dropping position of a preparation such as preparation containing milnacipran in the vessel, has an influence on the decomposition of the preparation, which is thought to slow down the elution of the drug from the preparation. Based on the elution testing method of the present invention, a stabilized design is created for the elution of a sugar-coated milnacipran tablet containing a composition in which milnacipran or a salt thereof is allowed to exist in a porous carrier as indicated above in 1.

To provide a concrete explanation of the elution test of this invention, when an elution test is performed in order to test a sugar-coated tablet which contains milnacipran, because the evaluation of the results must not be influenced by the falling position, it is desirable when the lower limit of the speed of revolutions of the paddle for the lower range is set from 75 rpm to 80 rpm, while 85 rpm is preferred. Although the upper limit is not particularly limiting, it is desirable when less than 200 rpm is used, preferably less than 150 rpm, while 100 rpm is particularly preferred. In addition, in the case when the number of the paddle revolutions must be set to 50 rpm during an elution test of a sugar-coated preparation containing milnacipran, a suitable evaluation value can be obtained with the Vankel vessel (made by the Vankel Company) which has a convex part preventing a sugar-coated film from falling directly below the rotary shaft of the paddle, so that the value is evaluated at the same time when the Vankel vessel is used with a disk having a suitable size which is deployed in the lowest part of the vessel. While the size of the disk is not particularly limiting, it is desirable when a round disk is used with a diameter in the range of 3~20 mm which has a height in the range of 3~15 mm, while a round disk having diameter in the range of 5~15 and a height in the range of 3~10 mm is preferred, and a round disk with a diameter of 8~12 mm and a height of 4~6 mm is particularly preferred. Although a PEAK vessel is not necessarily required and the presence of a disk is also not necessary when testing is performed using the paddle revolution speed above 75 rpm, testing can be performed with a PEAK vessel and when such a disk is present.

The present invention therefore provides an elution testing method enabling to stabilize the elution of a sugar-coated formulation of this invention containing milnacipran.

4. The present invention also provides a composition containing milnacipran and/or a preparation containing milnacipran which suppresses discoloration, as well as a composition containing milnacipran and/or a preparation containing milnacipran which suppresses changes of external appearance during storage. The composition containing milnacipran and/or a preparation containing milnacipran which suppresses changes of external appearance and discoloration can be obtained by combining pharmacologically acceptable additives which do not cause interaction due to passage of time with milnacipran. It is thus possible to add for example a granular preparation, a powder preparation or a tablet or with a similar form of preparation using other additive agents. While these additive agents are not particularly limited, it is desirable when the additives used for this combination are pharmacologically acceptable additives which do not cause an interaction with milnacipran with passage of time.

Desirable additives to milnacipran which do not cause an interaction due to passage of time include D-mannitol, cornstarch, partially pregelatinized starch, sodium carboxymethyl starch, lower-substituted hydroxy propyl cellulose, carmelose, or calcium hydrogen phosphate and other examples can be named. Particularly preferred are D-mannitol, cornstarch, partially pregelatinized starch, sodium carboxymethyl starch, or calcium hydrogen phosphate and other examples, while D-mannitol and calcium hydrogen phosphate are especially preferred. It is possible to use only one type of additives to milnacipran which do not cause an interaction due to passage of time, or two or more such additive types can be combined together, while one type is preferred. Moreover, it is preferred when separate modes are used if two or more additive types are used.

The "composition containing milnacipran" in "a milnacipran-containing composition which suppresses changes of external appearance during storage" can be also a composition in which milnacipran is present in a porous carrier as described above in 1., or it can be a composition in which milnacipran or a salt thereof is not present in a porous carrier, as no particular limitations are imposed on the presence or absence of milnacipran or a salt thereof in a porous carrier.

The discoloration indicated as an example of a change of external appearance can be determined by measuring the color difference ($\Delta E$) using a color-difference meter which measures the extent of the difference in color and the like. A difference in color can be perceived as a changed color tone if the difference exceeds 3.0 $\Delta E$ based on NBS units. In the case of a composition containing milnacipran, it is desirable when the $\Delta E$ value is less than 3.0 after the composition has been stored at 60° C. for a period of two weeks.

The following is a more detailed explanation of embodiments and comparative examples of this invention. However, this present invention is not limited in any way by these examples.

EMBODIMENTS

Each of the examples described below, from "Embodiment 1-1" to "Embodiment 1-11", relate to a milnacipran formulation manufactured using a preparation which contained milnacipran so that milnacipran or a salt thereof was present in a porous carrier.

Embodiment 1-1

After 150 g of milnacipran hydrochloride (manufactured by Pierre Fabre Company) were dissolved in 84 g of distilled water, 375 g of anhydrous calcium hydrogen phosphate manufactured with the spray-drying method (by the Fuji Chemical Industries Company, trade name Fuji Karin) were added, and after mixing-adsorption was performed in a V mixer for 30 minutes, the mixture was removed and dried by being set aside at 50° C. for 15 hours so that an adsorption powder was obtained through a mesh of 710 μm. 50 g of carmelose calcium (manufactured by the Gotoku Pharmaceuticals Company, trade name ECG-505) was added to 437.5 g of this adsorption powder, as well as 2.5 g of light anhydrous silicate (made by the Freunt Industries Company, trade name Adozolida 101), and after mixing was performed for a period of 10 minutes with a V mixer, 10 g of magnesium stearate was added (manufactured by Taihei Chemicals Company, trade name magnesium stearate), mixing was performed for 5 minutes and a tablet powder was obtained. This tablet powder was then crushed using the 8 R mortar and pestle and 100 mg of a tablet (raw table) which contained 25 mg of milnacipran hydrochloride were obtained.

Embodiment 1-2

After 150 g of milnacipran hydrochloride (manufactured by Pierre Fabre Company) was dissolved in 84 g of distilled water, 375 g o of anhydrous calcium phosphate, manufactured with the spray-drying method (made by the Fuji Chemicals Company, trade name Fujikarin) was atomized using a fluidized bed granulator while air was supplied at 40° C., so that after atomizing was completed, the temperature of supplied air was raised to 70° and drying was conducted until the temperature of the exhaust gas reached 40° C. After that, the powder substance was removed from the fluidized bed granulator, passed through a 710 μm mesh and an adsorption powder was obtained. 2.5 g of light anhydrous silicate (made by the Freunt Industries Company, trade name Adozolida 101) was added to 437.5 g of this adsorption powder and mixing was performed for a period of 10 minutes in a V mixture. In addition, 10 g of magnesium stearate was added (manufactured by Taihei Chemicals Company, trade name magnesium stearate) and a tablet powder was obtained. This tablet powder was than crushed using the 8 R mortar and pestle with the diameter of 6 mm and a 100 mg tablet (uncoated tablet) which contained 25 mg of milnacipran hydrochloride per 1 tablet was obtained.

Embodiment 1-3

After 25 g of milnacipran hydrochloride (manufactured by the Pierre Fabre Company) were dissolved in 14 g of distilled water, 62.5 g of porous magnesium silicate were added (manufactured by Kyowa Chemical Industries Company, trade name magnesium silicate), and after mixture-adsorption was performed for a period of 30 minutes with a V mixer, the mixture was removed and set aside to perform drying at 50° C. for 12 hours, passed through a mesh of 710 μm and adsorption powder was obtained. 10.5 g of lower-substituted hydroxy propyl cellulose (manufactured by the Shin-Etsu Chemical Industry Company, trade name LH-31) were added. After mixing was performed for 10 minutes with a V mixer, 2 g magnesium stearate was added (made by the Taihei Chemicals Company, trade name magnesium stearate) and mixing was performed for 5 minutes. This mixture was then creased using the 8 R mortar and pestle with a diameter of 6 mm and a tablet was prepared so that 25 mg of milnacipran was contained per 1 tablet in a 100 mg tablet (uncoated tablet).

Embodiment 1-4

After 25 g of milnacipran hydrochloride (made by Pierre Fabre Company) were dissolved in 14 g of distilled water and added to 62.5 g of porous calcium silicate (made by the Eisai Company, trade name FlowRight RE) and mixing and adsorption was performed with a V mixer for 30 minutes, the mixture was removed and left stand at 50° C. to perform drying for a period of 12 hours, passed through a 710 μm mesh and adsorption powder was obtained. To this adsorption powder was then added 10.5 g of lower-substituted hydroxy propyl cellulose (made by the Shin-Etsu Chemical Industry Company, trade name LH-31), and after mixing was performed with a V mixer for 10 minutes, 2 g of magnesium stearate were added (made by the Taihei Chemicals Company, trade name magnesium stearate), mixing was performed for 5 minutes and the mixture was then crushed using the 12 R mortar and pestle with a diameter of 8 mm to obtain a tablet so that a 100 mg tablet (uncoated tablet) was obtained which contained mg of milnacipran hydrochloride per 1 tablet.

Embodiment 1-5

After 67 g of hydroxy propyl methyl cellulose (made by the Shin-Etsu Chemicals Company, trade name TC-5RW) were dissolved in 875 ml of distilled water and g of talc (manufactured by the Hayashi Kasei Company) was dispersed in it together with 10 g of titanium oxide (manufactured by the Wako Pure Chemical Industries Company, trade name titanium dioxide), 33.35 g of an aqueous dispersion of ethyl cellulose (made by Asahi Kasei Company, trade name Aqua Coat), and 8 g of triethyl citrate (made by the Morimura Shoji Company, trade name Citroflex 2) were added to create a dispersed solution so that the tablet obtained in Embodiment 1-1 was coated with 5 mg of the solution using a coating device (Doria coater DRC-300, made by the Powrex Company) and 1 coated tablet containing 105 mg was obtained.

Embodiment 1-6

67 g of hydroxy propyl methyl cellulose (made by the Shin-Etsu Pure Chemicals Company, trade name TC-5RW) were dissolved in 875 ml of distilled water), and 30 g of talc (manufactured by the Hayashi Kasei Company) was dispersed in it together with 10 g of titanium oxide (manufactured by the Wako Pure Chemical Industries Company, trade name titanium dioxide), 33.35 g of an aqueous dispersion of ethyl cellulose (made by Asahi Kasei Company, trade name Aqua Coat), and 8 g of triethyl citrate (made by the Morimura Shoji Company, trade name Citroflex 2) were added to create a dispersed solution and the tablets obtained in Embodiment 1-2 was coated with 5 mg of the solution using a coating device (Doria coater DRC-300, made by the Powrex Company) and 1 coated tablet was containing 105 mg was obtained.

Embodiment 1-7

125 g of milnacipran (made by Pierre Fabre Company) were dissolved in 70 mg of distilled water and 315 g of anhydrous calcium hydrogen phosphate manufactured with the spray-drying method (made by the Fuji Chemical Industries Company, trade name Fujikarin) were atomized while air having the temperature of 40° C. was supplied using a fluidized bed granulator. After the atomizing was finished, the temperature of the supplied air was raised to 70° C. and drying was performed until the temperature of the exhaust gas reached 40° C. After that, the powder was removed from the fluidized bed atomizer, passed through a mesh of 710 μm and a powder formulation was obtained.

Embodiment 1-8

No. 4 gelatin capsule (made by Shionogi Qualicaps, trade name Qualicaps gelatin) was filled with 100 mg of the tablet powder obtained in Embodiment 1-1 so that a capsule preparation was obtained which contained 25 mg of milnacipran hydrochloride per 1 capsule.

Embodiment 1-9

No. 4 HPMC capsule (made by Shionogi Qualicaps, trade name QUALI-V) was filled with the tablet powder obtained in Embodiment 1-1 so that a capsule preparation was obtained which contained 25 mg of milnacipran hydrochloride per 1 capsule containing 100 mg.

Embodiment 1-10

No. 3 gelatin capsule (made by the Shionogi Qualicaps Company, trade name Qualicaps gelatin) was filled with 100 mg of the tablet powder obtained in Embodiment 1-2 so that a capsule preparation was obtained which contained 25 mg of milnacipran hydrochloride per 1 capsule.

Embodiment 1-11

No. 3 HPMC capsule (made by the Shionogi Qualicaps Company, trade name QUALI-V) was filled with 100 mg of the tablet powder obtained in Embodiment 1-2 so that a capsule preparation was obtained which contained 25 mg of milnacipran hydrochloride per 1 capsule.

Comparative Example 1-1

125 g of milnacipran chloride (made by Pierre Fabre Company), 312.5 g of anhydrous calcium hydrogen phosphate (made by the Kyowa Chemicals Company, trade name anhydrous calcium hydrogen phosphate GS), and 25 g of carmelose calcium (manufactured by the Gotoku Pharmaceuticals Company, trade name ECG-505) was placed into a high speed mixer (made by Fukae-Powtec), mixing was performed for 3 minutes with a blade rotational speed of 670 rpm and a cross screw rotational speed of 2,000 rpm, 30 g of 50% ethanol aqueous solutions were added and mixing was then conducted using the same blade rotational speed and cross screw rotational speed to perform mixing and granulation.

This mixture was placed into a fluidized bed granulator (made by Powtec, LAB-1), drying was conducted while the temperature of supplied air was at 80° C., the mixture was removed at the point when the temperature of 50° C. was created for exhaust gas and the mixture was adjusted with a mesh of 850 μm. To this mixture was then added 25 g of carmelose calcium (made by the Gotoku Pharmaceutical Company, trade name ECG-505) and 2.5 g of light anhydrous silicate (made by the Freunt Industries Company, trade name Adozolida 101) were added and the mixing was performed for 10 minutes in a V mixer. In addition, 10 g of magnesium stearate (made by the Taihei Chemicals Company, trade name magnesium stearate) were added, mixing was performed for 5 minutes and tablet powder was obtained.

Comparative Example 1-2

The tablet obtained in Comparative Example 1-1 (uncoated tablet) was dissolved in 1,750 g of distilled water with 134 g of hydroxy propyl methyl cellulose (made by the Shin-Etsu Chemicals Company, trade name 5RW), 60 g of talc (made by the Hayashi Kasei Company), and 20 g of titanium oxide (made by the To a Titanium Company, trade name titanium dioxide) was added, as well as 66.7 g of ethyl cellulose aqueous solution (made by the Asahi Kasei Company, trade name Aqua Coat) and 16 g of a dispersed solution of triethyl citrate (made by the Pfizer Pharmaceuticals Company, trade name Citroflex) was used to create a dispersed solution and the tablet obtained in Embodiment 1-1 was coated with 5 mg of the solution using a coating device (Doria coater DRC-300, made by the Powrex Company) and 1 coated tablet containing 105 mg was obtained.

Comparative Example 1-3

A high-speed mixer (made by the Fukae Powtec Company) was charged with 125 g of milnacipran hydrochloride (made by Pierre Fabre Company) and with 315 g of anhydrous calcium hydrogen phosphate in the shape of fine particles (made by the Kyowa Chemicals Company, trade name anhydrous calcium hydrogen phosphate GS), mixing was performed for 3 minutes using 670 rpm for the number of revolutions of the rotary blade and with a cross screw rotational speed of 2,000 rpm, 30 g of distilled water were added to this mixture and mixing was then performed using the same number of revolutions for the rotary blade and for the cross screw for 3 minutes to obtain granulated material. This granulated material was then set aside to dry at 50° C. for 8 hours, passed through a 710 μm mesh and a powder preparation was obtained.

Comparative Example 1-4

175 g of milnacipran hydrochloride (made by the Pierre Fabre Company), 204.4 g of anhydrous calcium hydrogen phosphate in the form of fine particles (made by the Kyowa Chemicals Company, trade name anhydrous calcium hydrogen phosphate AGS), and 16.1 g of carmelose calcium (made by the Gotoku Pharmaceuticals Company, trade name ECG-505) were loaded into a high-speed mixer (made by the Fukae Powtec Company) and mixing was performed for 3 minutes using 670 rpm for the number of revolution of the blade and 2,000 rpm for the number of revolutions of the cross screw, 30 g of a 50% ethanol aqueous solution were added, and after stirring was performed using the same number of revolutions for the blade and for the cross screw for 3 minutes, a granulated substance was obtained. This substance was then loaded into a fluidized bed granulator (made by the Powtec Company, LAB-1) and drying was performed while the temperature of supplied air was set to 80° C. so that the mixture was removed at the point when the temperature of 50° C. was created for the exhaust gas, the mixture was then passed through a mesh of 850 μm and adjusted granules were prepared. 16.1 g of carmelose calcium (made by the Gotoku Pharmaceuticals Company, trade name ECG-505) was then added to this granulated powder, 1.4 g of light anhydrous silicate was added (made by the Freunt Industries Company) Adozolida 101), and mixing was performed in a V mixer for 15 minutes. In addition, 7 g of magnesium stearate were added (made by the Taihei Chemicals Company, trade name magnesium stearate), mixing was performed for a period of 5 minutes and a capsule filling powder was obtained. No. 4 gelatin capsule was than filled with 100 mg of this powder (made by the Shionogi Qualicaps Company, trade name Qualicaps gelatin), and a capsule preparation was obtained which contained 25 mg of milnacipran hydrochloride per 1 tablet.

Comparative Example 1-5

No. 3 gelatin capsules filled with 100 mg of the filling powder obtained in Comparative Example 1-4 (made by the Shionogi Qualicaps Company, trade name Qualicaps gelatin), so that a capsule preparation was obtained which contained 25 mg of milnacipran per 1 capsule filled with 100 mg.

The embodiments described below (in Embodiment 2-1 and Embodiment 2-2) relate to a preparation in which an HPMC capsule was filled with a mixed powder which did not contain a powder carrier, to a preparation in which a gelatin capsule was filled with a composition containing milnacipran in which a milnacipran sale was present in a porous carrier (in Embodiment 2-3), and a preparation in which an HPMC capsule was filled with a composition containing milnacipran in which a milnacipran salt was present in a porous carrier (in Embodiment 2-4).

Embodiment 2-1

175 g of milnacipran salt (made by Pierre Fabre Company), 204.4 g of anhydrous calcium hydrogen phosphate in the form of fine particles (made by the Kyowa Chemicals Company, trade name anhydrous calcium hydrogen phosphate), and 16 g of carmelose calcium (made by the Gotoku Pharmaceuticals Company, trade name ECG-505) were loaded into a high-speed mixer (made by the Fukae Powtec Company), mixing was performed for 3 minutes using the rotational speed of 670 rpm for the blade and the rotational speed of 2000 rpm for the cross screw, 30 g of 50% ethanol aqueous solution were added to this mixture and stirring was performed while the same rotational speed was used for the number of revolutions of the blade and for the number of revolutions of the cross screw to prepare a granulated substance. This substance was then fed into a fluidized bed granulator (made by the Powtec Company, LAB-1) and drying was performed while the temperature of supplied air was at 80° C., the mixture was removed at the point when the temperature of the exhaust gas reached 50° C. and the mixture was passed through a mesh of 850 μm and adjusted granules were prepared. 16.1 g of carmelose calcium were then added to this granulated substance (made by the Gotoku Pharmaceuticals Company, trade name ECG-505), 1.4 g of light anhydrous silicate were added (made by the Freunt Company, trade name Adozolida 101) and mixing was performed for 15 minutes with a V mixer. In addition, 7 g of magnesium stearate were added (made by the Taihei Chemicals Company, trade name magnesium stearate), mixing was performed for 5 minutes and a capsule filling powder was obtained. No. 4 HPMC capsules (made by the Shionogi Qualicaps Company, trade name QUALI-V) were then filled with 100 g of this powder so that a capsule preparation was obtained which contained 25 mg of milnacipran hydrochloride per 1 capsule.

Embodiment 2-2

No. 3 HPMC capsule (made by the Shionogi Qualicaps Company, trade name QUALI-V) was filled with 100 mg of the capsule preparation obtained in Embodiment 2-1 so that a capsule preparation was obtained which contained 25 mg of milnacipran hydrochloride per 1 capsule.

Embodiment 2-3

150 g of milnacipran hydrochloride (made by Pierre Fabre Company) were dissolved in 84 g of distilled water, and 375 g of anhydrous calcium hydrogen phosphate manufactured with the spray-drying method was atomized when the temperature of the supplied air was 40° C. using a fluidized bed granulator (made by the Fuji Chemicals Company, trade name Fujikarin). After the atomizing was finished, the temperature of supplied air was raised to 70° C. and drying was performed until the temperature of 40° C. was created for exhaust gas. After that, the powder was removed from the fluidized bed granulator, passed through a 710 μm mesh and adsorption powder was obtained. 50 g of carmelose calcium (made by the Gotoku Pharmaceuticals Company, trade name ECG-505) was then added to 437.5 g of this adsorption powder, 2.5 g of light anhydrous silicate (made by the Freunt Industries Company, trade name Adozolida-101) were added and mixing was performed with a V mixer for 10 minutes. In addition, 10 g of magnesium stearate (made by the Taihei Chemicals Company, trade name magnesium stearate) were added, mixing was performed for 5 minutes and a tablet powder was obtained. No. 3 gelatin capsule (made by the Shionogi Qualicaps Company, trade name Qualicaps gelatin) was filled with 100 mg this powder so that a capsule preparation was obtained which contained 25 mg of milnacipran hydrochloride per 1 capsule.

Embodiment 2-4

No. 3 HPMC capsule (made by the Shionogi Qualicaps Company, trade name QUALI-V) was filled with 100 mg of the tablet powder obtained in Embodiment 2-3 so that a capsule preparation was prepared which contained 25 mg of milnacipran per 1 capsule.

Comparative Example 2-1

No. 4 gelatin capsule (made by the Shionogi Qualicaps Company, trade name Qualicaps gelatin) was filled with 100 mg of the capsule powder obtained in Embodiment 2-1 so that a capsule preparation was obtained which contained 25 mg of milnacipran hydrochloride per 1 capsule.

Comparative Example 2-2

No. 3 HPMC capsule (made by the Shionogi Qualicaps Company, trade name Qualicaps gelatin) was filled with 100 mg of the tablet powder obtained in Embodiment 2-1 so that a capsule preparation was prepared which contained 25 mg of milnacipran per 1 capsule.

The embodiments below (Embodiment 3-1) and (Embodiment 3-2) relate to a sugar-coated tablet.

Embodiment 3-1

240 g of milnacipran hydrochloride (made by Pierre Fabre Company) were dissolved in 134.4 g of distilled water, and 280.32 g anhydrous calcium hydrogen phosphate prepared with the spray-dry method was atomized in a fluidized bed granulator (made by the Fuji Chemicals Company, trade name Fujikarin) using 40° C. for the temperature of supplied air. After the atomizing was finished, the temperature of supplied air was raised to 70° C. and drying was performed until the temperature of exhaust gas reached 40° C. After that, the tablet powder was removed from the granulator, passed through a 710 μm mesh and adsorption powder was obtained. 36.8 g of carmelose calcium (made by the Gotoku Pharmaceuticals Company, trade name ECG-505) was then added to 433.6 g of this adsorption powder, 1.6 g of light anhydrous silicate was added (made by the Freunt Company, trade name Adozolida 101), mixing was performed for 10 minutes with a V mixer, 8 g of magnesium stearate was added (made by the Taihei Chemistry Company, trade name magnesium stearate) mixing was performed for 5 minutes and a tablet powder was obtained. This tablet powder was then crushed with the 3.5 R mortar pestle which had a diameter of 5 mm and a 60 mg tablet was obtained (uncoated tablet) which contained 25 mg of milnacipran tablet.

A coater (made by the Powrex Company, Doria Coater DRC-300) was charged with 326 g of the uncoated tablet obtained in this manner, and after 88 g of hydroxyl propyl methyl cellulose 2910 (made by the Shin-Etsu Chemical Industries Company, trade name TC-5R) were dissolved in 1,169.2 g of distilled water, 22 g of titanium dioxide (made by the Wako Pure Chemicals Company, trade name titanium dioxide) were added and the mixture was adjusted by being homogeneously dispersed in a homogenous mixer to prepare a film solution which was atomized inside a film coater so that a film tablet was obtained which contained 10 mg of the film layer weight amount per the tablet preparation weight of 70 mg. The film tablet prepared in this manner was then coated in a sugar coating device (made by the Kikusui Seisakujo Company) with a sugar coating solution (hydroxyl propyl methyl cellulose 2208, made by the Shin-Etsu Chemical Industries Company, trade name SB-4), 1,050 ml of distilled water was added and dissolution was induced. Next, 630 g of white sugar (made by the Shin Mitsui Seito Company, trade name AA) was added, 350 g of precipitated calcium carbonate were added (made by the Bihoku Funka Industries Company, product name precipitated calcium carbonate, prepared with thorough stirring) and after the mixture was supplied dropwise using 3 ml/one portion, and the sugar-coating solution was used for sugar coating performed in a homogeneous manner. Next, air was blown into the device (temperature: 60° C.) and drying of the tablet preparation was performed for 3 minutes. These operations were repeated until the amount was increased to 30 mg per tablet in order to form a sugar-coating layer. Next, 700 g of a sugar coating solution (made by Shin Mitsui Seito Company, trade name AA) was added to 470 g of distilled water and after dissolution was induced to adjust the solution, homogeneous coating was performed dropwise with the sugar solution using about 3 ml/1 portion. Next, an air current was introduced (temperature: 60°) into the operation so that the tablet solution was dried for a period of 3 minutes. These operations were repeated until the amount was increased to 20 mg per 1 tablet so that a sugar-coated tablet was obtained with a tablet preparation weight of 120 mg per 1 tablet.

Embodiment 3-2

360 g of milnacipran hydrochloride (made by Pierre Fabre Company) were dissolved in 201.6 g of distilled water, 907.2 g of porous anhydrous calcium hydrogen phosphate, prepared with the spray-drying method, were atomized using a fluidized bed granulator (made by the Fuji Chemical Industries Company, trade name Fujikarin) while an air current was supplied at 40° C. After the atomizing was finished, the temperature of supplied air was increased to 70° C. and drying was conducted until the exhaust gas temperature was 40° C. After that, the powder was removed from the fluidized bed granulator, passed though a 710 µm mesh and an adsorption powder was obtained. 120 g of carmelose calcium (made by the Gotoku Pharmaceuticals Company, trade name ECG-505) was added to 1,056 g of this adsorption powder, mixing was performed for 10 minutes with a V mixer, 24 g of magnesium stearate (made by the Taihei Chemicals Company, trade name magnesium stearate) were added, mixing was conducted for 5 minutes and a tablet powder was obtained. This tablet powder was then crushed with the 4.5 R mortar and pestle with a diameter of 6 mm so that a tablet preparation (uncoated tablet) was obtained which contained 25 mg of milnacipran hydrochloride per 100 mg of the tablet.

500 mg of this obtained uncoated table was placed into a coating device (made by the Powrex Company, Doria DRC-300), and after 40 g of hydroxyl propyl methyl cellulose 2910 (made by the Wako Pure Chemicals Company, trade name TC-5R) were dissolved in 531.6 g of distilled water, 60 g of titanium oxide (made by the Wako Pure Chemicals Industries Company, trade name titanium oxide) were added and a homogeneous dispersion was induced with a homogeneous mixer, and an adjusted film solution was obtained which was atomized in a film coating device so that a film tablet was obtained in which the tablet weight was 105 mg, while the weight of the film layer was 5 mg per 1 tablet.

The film tablet obtained in this manner was placed into a coating device (made by the Powrex Company, Doria Coater DRC-300) with a sugar coating solution (hydroxyl propyl methyl cellulose 2208, made by the Shin-Etsu Chemical Industries Company, trade name SB-4), and dissolved in 1,050 ml of added distilled water. Next, 630 g of white sugar (made by the Shin Mitsui Seito Company, trade name AA) was added and after dissolution, 350 g of precipitated calcium carbonate was added (made by the Bihoku Funka Industries Company, trade name precipitated calcium carbonate) and the mixture was adjusted with thorough stirring so that atomizing was performed for 2 minutes with about 3 ml/one portion and homogenous coating was performed with the sugar solution without supplying air. Next, air was supplied (temperature: 70° C.) into the atomizer so that the tablet preparation was dried for a period of 3 minutes. These operations were repeated until the amount was increased to 30 mg per 1 tablet and a sugar coating layer was formed. Next, 700 g of a sugar solution (white sugar, made by the Shin Mitsui Seito Company, trade name AA) was added to 470 g of distilled water and dissolution was induced to adjust the solution, atomizing was performed with about 3 ml/minute for a period of 2 minutes so that a homogeneous coating was formed with the sugar solution without supplying air. Next, air was supplied (temperature: 70° C.) and the tablet preparation was dried for a period of 3 minutes. These operations were repeated until the amount was increased to 20 mg per 1 tablet so that a sugar-coated tablet was obtained which had the tablet preparation weight of 155 mg per 1 tablet.

Comparative Example 3-1

175 g of milnacipran hydrochloride (made by Pierre Fabre Company), 204.4 g of anhydrous calcium hydrogen phosphate in the form of fine particles (made by the Kyowa Chemicals Company) and 16.1 g of carmelose calcium (made by the Gotoku Pharmaceuticals Company, trade name ECG-505) were fed into a high-speed mixer (made by the Fukae Powrex Company), mixing was performed for 3 minutes using 670 rpm for the number of revolutions of the blade and 2,000 rpm for the number of revolutions of the cross screw, 30 g of an aqueous ethanol solution were added and while the mixture was mixed using the same number of revolutions for the blade and for the cross screw, the mixture was stirred and granulated for 3 minutes. This mixture was then fed into a fluidized bed granulator (made by the Powrex Company, LAB-1), dried with air supplied at 80° C. and removed at the point when the exhaust gas temperature reached 50° C., and the mixture was passed through a mesh of 850 µm and granulated. 16.1 g of carmelose calcium (made by the Gotoku Pharmaceuticals Company, trade name ECG-505) were then added to this granulated powder, 1.4 g of light anhydrous silicate (made by the Freunt Industries Company, trade name Adozolida) were added, mixing was performed with a V mixer for 15 minutes, and 8 g of magnesium stearate (made by the Taihei Chemicals Company, trade name magnesium stearate) were added, mixing was conducted for a period of 5 minutes and a tablet powder was obtained. This powder was then crushed with the 3.5 R mortar and pestle to prepare a tablet (uncoated tablet) which contained 25 mg of milnacipran hydrochloride per 1 tablet with a weight of 60 mg.

300 g of the obtained uncoated tablet was fed into a coater (made by the Powrex Company, Doria Coater DRC-300), and after 60 g of hydroxy propyl methyl cellulose 2910 (made by the Shin-Etsu Chemical Industries Company, trade name TC-5R) was dissolved in 1,050 ml of distilled water, 15 g of titanium oxide (made by the Wako Pure Chemical Industries, trade name titanium oxide) were added, homogeneous dispersion was induced with a homogenous mixer, a film solution was prepared, the solution was atomized in a film coater and a film tablet was prepared with a tablet weight of 70 mg having a film layer which weighed 10 mg.

The film tablet obtained in this manner was fed into a coater (made by the Powrex Company, Doria Coater DRC-300), was dissolved in a sugar coating solution (hydroxy propyl methyl cellulose 2208, made by the Shin-Etsu Chemical Industries Company, trade name SB-4) and 1,050 ml of distilled water was added. Next, 630 g of white sugar (made by the Shin Mitsui Seito Company, trade name AA) were added and dissolution was induced. In addition, 350 g of precipitated calcium carbonate were added (made by the Bihoku Funka Kogyo Company, trade name precipitated calcium carbonate), and after thorough stirring was performed to adjust the mixture, atomizing was conducted with about 3 ml/minute so that a homogenous coating with the sugar coating solution was performed without supplying air. Next, air was supplied (temperature: 70° C.) and the tablet formulation was dried for 3 minutes. These operations were repeated until the amount per 1 tablet was increased to 30 mg and a sugar coating layer was formed. Next, 470 g of distilled water was added to 700 g of a sugar solution (white sugar, made by the Shin Mitsui Seito Company, trade name AA) and dissolution was induced and atomizing was performed for 2 minutes with about 3 ml/minute so that homogeneous coating with the sugar solution was achieved without supplying air. Next, air was supplied (temperature: 70° C.) and the tablet formulation was dried for 3 minutes. These operations were repeated until the amount was increased to 20 mg per 1 tablet so that a sugar-coated tablet was obtained in which the tablet weight was 120 mg per 1 tablet.

Comparative Example 3-2

175 g of milnacipran hydrochloride (made by the Pierre Fabre Company) and 441 g of anhydrous calcium hydrogen phosphate in the form of fine particles (made by the Kyowa Chemicals Company, trade name anhydrous hydrogen phosphate GS) were fed into a high-speed mixer (made by the Fukae Powrex Company) and mixing was performed for 3 minutes using 670 rpm for the number of revolutions of the blade and 2,000 rpm for the number of revolutions of the cross screw, 40 g of aqueous ethanol solution were added and while the mixture was mixed using the same number of revolutions for the blade and for the cross screw, the mixture was stirred and granulated for 3 minutes. This mixture was then fed into a fluidized bed granulator (made by the Powrex Company, LAB-1), dried with air supplied at 80° C. and removed at the point when the exhaust gas temperature reached 50° C., the mixture was passed through a mesh of 850 μm and granulated. 70 g of carmelose calcium (made by the Gotoku Pharmaceuticals Company, trade name ECG-505) were then added to this granulated powder, mixing was performed with a V mixer for 15 minutes and 14 g of magnesium stearate were added (made by the Taihei Chemicals Company, trade name magnesium stearate), mixing was performed for 15 minutes and a tablet powder was obtained. This tablet powder was crushed using the 4.5 R mortar and pestle and 100 mg a tablet formulation (uncoated tablet) was obtained which contained 25 mg of milnacipran hydrochloride per 1 tablet.

550 mg of the obtained uncoated tablet was then put into a coater (made by the Powrex Company, Doria Coater DRC-300) and after 48 g of hydro propyl methyl cellulose 2910 (made by the Shin-Etsu Chemical Industries Company, trade name TC-5R) were dissolved in 637.8 g of distilled water, 72 g of titanium oxide (made by the Wako Pure Chemicals Company, trade name titanium oxide) were added and after homogeneous dispersing was induced with a homogeneous mixer, the adjusted film solution was atomized in a film coating device so that a film formulation was obtained which contained a film layer weighing 5 mg per 1 tablet which had a weight of 105 mg.

1,050 ml of distilled water was added to the sugar solution (hydroxy propyl methyl cellulose 2208, made by the Shin-Etsu Chemical Industries Company, trade name SB-4) in a sugar coater (made by the Kikusui Seisakujo Company) with the obtained film tablet and dissolution was induced. Next, 630 g of white sugar (made by the Shin Mitsui Seito Company, trade name AA) were added and dissolution was induced. In addition, 350 g of precipitated calcium carbonate (made by the Bihoku Funka Kogyo Company, trade name precipitated calcium carbonate) were added and after thorough stirring was performed to adjust the mixture, a sugar coating solution was added dropwise with about 3 ml/portion and homogenous coating was performed with the sugar coating solution. Next, air was supplied (temperature: 60° C.) and the tablet formulation was dried for 3 minutes. These operations were repeated until the amount was increased to 30 mg and a sugar coating layer was formed. Next, 470 g of distilled water was added to 700 g of a sugar solution (white sugar, made by the Shin Mitsui Seito Company, trade name AA), dissolution was induced to adjust the mixture and about 4 ml/portions were formed dropwise so that homogenous coating was performed with the sugar solution. Next, air was supplied (temperature: 60° C.), and the tablet formulation was dried for a period of 3 minutes. These operations were repeated until the amount was increased to 20 mg per 1 tablet so that a sugar-coated tablet was obtained with a tablet weight of 155 mg per 1 tablet.

Embodiment 4-1

10 g of milnacipran hydrochloride (made by the Pierre Fabre Company) were mixed for a period of 3 minutes using a chemical grinder with 10 g of an additive and a powder formulation was obtained. 1 g of this obtained powder formulation was then placed into a glass bottle, a lid was attached so that a hermetically sealed status was created and the formulation was stored at 60° C. Table 1 shows the changed in external appearance after the formulation was stored for a period of 2 weeks.

TABLE 1

| No. | Additive | Before the Storage | After the Storage |
|-----|----------|--------------------|--------------------|
| 1 | D-Mannitol | White color | White color |
| 2 | Corn starch | White color | White color |
| 3 | Partially pregelatinized starch | White color | White color |
| 4 | Sodium carboxymethyl starch | White color | White color |
| 5 | Lower-substituted hydroxy propyl cellulose | White color | White color |
| 6 | Carmelose | White color | White color |
| 7 | Calcium hydrogen phosphate | White color | White color |

The additive formulation and 1 g of milnacipran hydrochloride formulation shown in Table 1 were placed into a powder measuring cell and when the color difference (ΔE) was measured with a color-difference meter which was provided with a 30 mm condenser lens (CLR-7100F, made by the Shimadzu Seisakujo Company), it was determined that there were no changes in the external appearance after the storage as the resulting ΔE was below 3.0 in each case.

Test Example 1-1

The tablet preparations obtained in Embodiment 1-1, Embodiment 1-2, Embodiment 1-3, Embodiment 1-4 and Comparative Example 1-1 were placed into a glass desiccator which had a diameter of 15 cm, a depth of 15 cm and which contained a saturated aqueous solution of potassium nitric acid and stored there at 30° C. for a period of 24 hours. The relative humidity in the desiccator at this time was about 92%.

After the storage, the tablet preparations were placed on a smooth glass plate which was free of irregularities, the plate was then gradually tilted and the slipping and falling angle of the tablet preparation was measured. In addition, the changes in the overall external appearance after the storage were also measured. As one can clearly see from the results shown in Table 1, the preparations that were mixed with additives other than the milnacipran additive, which were contained in Comparative Example 1-1, eventually became stuck to the glass plate when measurements of the preparations obtained after granulated tablets were produced were performed after storage at 30° C. and with a relative humidity of 92%, while slipping and falling did not occur even when the plate was tilted again from the horizontal position by 90°.

In contrast to that, the tablet preparation of Embodiment 1-1 and of Embodiment 1-2, which contained milnacipran hydrochloride adsorbed in porous anhydrous calcium hydrogen phosphate manufactured with the spray-drying method, the tablet preparation containing milnacipran hydrochloride adsorbed in porous magnesium silicate prepared in Embodiment 1-3, and the tablet preparation containing milnacipran hydrochloride adsorbed in porous material prepared in Embodiment 1-4 did not display the phenomenon wherein sticking of the tablet preparation to the glass plate occurred as was the case in Comparative Example 1-1 and slipping and falling occurred in each case with a tilting angle below 40°.

In addition, while the tackiness and other characteristics relating to changes of external appearance were confirmed after the storage of the tablet preparation of Comparative Example 1-1, no changes of external appearance of the tablet preparation were ascertained in Embodiment 1-1, Embodiment 1-2, Embodiment 1-3, and Embodiment 1-4.

TABLE 2

| | Before the Storage | After the Storage | Changes of External Appearance After the Storage |
|---|---|---|---|
| Embodiment 1 - 1 | 16° | 34° | No changes in external appearance when compared to the status before the storage. |
| Embodiment 1 - 2 | 16° | 33° | No changes in external appearance when compared to the status before the storage |
| Embodiment 1 - 3 | 18° | 24° | No changes in external appearance when compared to the status before the storage |
| Embodiment 1 - 4 | 18° | 23° | No changes in external appearance when compared to the status before the storage |
| Comp. Example 1 - 1 | 14° | >90° | The tablet preparation was sticky compared to the status before the storage. |

Test Example 1-2

The film-coated tablets obtained in Embodiment 1-5, Embodiment 1-6 and Comparative Example 1-2 were placed into a glass desiccator which had a diameter of 15 cm with a depth of 15 cm and which contained a saturated aqueous solution of potassium nitric acid and they were stored there at 30° C. for a period of 24 hours. The relative humidity in the desiccator at this time was about 92%.

After the storage, the tablet preparations were placed on a smooth glass plate which was free of irregularities, the plate was then gradually tilted and the slipping and falling angle of the tablet preparation was measured. In addition, changes of the external appearance after the storage were observed. Table 3 shows the results.

After the film-coated preparations in tablet preparation obtained after granulation of tablets which were mixed with other additives other than milnacipran chloride in Comparative Example 1-2 were stored at 30° C. with a relative humidity of 92%, the preparations stuck to the glass plate used when the measurement was conducted and the slipping and falling did not occur even when the glass plate was tilted from the horizontal position by 90° C.

On the other hand, the phenomenon wherein strong adhesion to the glass plate occurred, as was the case with the tablet preparation of Comparative Example 1-2, did not occur in Embodiment 1-5 and in Embodiment 1-6, which were prepared as film-coated tablets in which milnacipran hydrochloride was adsorbed in porous anhydrous calcium hydrogen phosphate according to the spray-drying method, and slipping and falling occurred in each case with a tilting angle of less than 50°.

In addition, while changes of external appearance such as peeling of the film when the tablet was touched with a finger were confirmed after the storage of the tablets obtained in Comparative Example 1-2, no changes of external appearance were ascertained with the film-coated tablets of Embodiment 1-5 and of Embodiment 1-6.

TABLE 3

| | Before the Storage | After the Storage | Changes of External Appearance After the Storage |
|---|---|---|---|
| Embodiment 1 - 5 | 13° | 45° | No changes in external appearance when compared to the status before the storage. |
| Embodiment 1 - 6 | 16° | 46° | No changes in external appearance when compared to the status before the storage |
| Comp. Ex. 1 - 2 | 20° | >90° | The tablet preparation was sticky compared to the status before the storage and peeling of the film occurred when the tablet preparation was touched with a finger. |

Embodiment 1-3

The powder preparations obtained in Embodiment 1-7 and in Comparative Example 1-3 were placed into a glass desiccator which had a diameter of 15 cm with a depth of 15 cm and which contained a saturated aqueous solution of potassium nitric acid and they were stored there at 30° C. for a period of 2 days. The relative humidity in the desiccator at this time was about 92%. After the storage, the repose angle of the powder preparations was calculated based on the cylindrical rotation method with three wheels. In addition, the changes in the external appearance of the stored powder preparations were also observed. Table 4 shows the result.

While there were no changes in the repose angle before and after the powder preparation of Embodiment 1-7 was stored using a temperature of 30° and a relative humidity of 92%, when the powder preparation of Comparative Example 1-3 was stored using a temperature of 30° C. and a relative humidity of 92%, the repose angle was clearly increased and the fluidity of the powder preparation deteriorated.

In addition, while no changes of external appearance were confirmed in Embodiment 1-7, coagulation was confirmed in the case of Comparative Example 1-3.

TABLE 4

|  | Before the Storage | After the Storage | Changes of External Appearance After the Storage |
|---|---|---|---|
| Embodiment 1-7 | 35° | 35° | No changes in external appearance when compared to the status before the storage. |
| Comp. Ex. 1-3 | 43° | 68° | Coagulation was confirmed and fluidity deteriorated compared to the status before the storage. |

Embodiment 1-4

The capsule formulations obtained in Embodiment 1-8, Embodiment 1-9 and Comparative Example 1-4 were placed into a glass desiccator which had a diameter of 15 cm with a depth of 15 cm and which contained a saturated aqueous solution of potassium nitric acid and they were stored there at 30° C. for a period of 2 days. The level of the relative humidity in the desiccator was about 92%.

After and before the storage, a metal disk with a diameter of about 6 mm was used to evaluate the presence or absence of cracks occurring when compression was applied with the pressure of 5 kg in the direction of the shorter diameter of the capsule and the ratio of the cracks was determined. In addition, the changes of external appearance after the storage were also observed. Table 5 shows the results. While no damage was observed with any of the 10 capsules that were manufactured in Embodiment 1-8 and Embodiment 1-9, all 10 capsules manufactured in Comparative Example 1-4 were damaged and it was also confirmed that the capsules were sticky.

TABLE 5

|  | Before the Storage | After the Storage | Change of External Appearance after the Storage |
|---|---|---|---|
| Embodiment 1-8 | 0% | 0% | There were no changes in external appearance compared to the status before the storage. |
| Embodiment 1-9 | 0% | 0% | There were no changes in external appearance compared to the status before the storage. |
| Comp. Example 1-4 | 0% | 100% | The capsule was sticky when compared to the status before the storage. |

Test Example 1-5

The capsule formulations obtained in Embodiment 1-10, Embodiment 1-11 and Comparative Example 1-5 were placed into a glass desiccator which had a diameter of 15 cm with a depth of 15 cm and which contained a saturated aqueous solution of potassium nitric acid and they were stored there at 30° C. for a period of 8 days. The level of the relative humidity in the desiccator at this time was about 92%.
[page 33]
The capsule preparation was placed on a smooth glass plate free that was of irregularities and the plate was gradually tilted so that the angle at which the capsule preparation turned over and fell was measured before and after the storage. In addition, the changes in the external appearance after the storage were also observed. Table 6 shows the results.

TABLE 6

|  | Before the Storage | After the Storage | Changes of External Appearance after the Storage |
|---|---|---|---|
| Embodiment 1-10 | 6° | 16° | There were no changes in the external appearance compared to the status before the storage. |
| Embodiment 1-11 | 6° | 4° | There were no changes in the external appearance compared to the status before the storage |
| Embodiment 1-5 | 6° | 57° | The capsule was sticky when compared to the status before the storage. |

Test Example 1-6

Elution tests were performed with the capsule preparations obtained in Embodiment 1-10, Embodiment 1-11 and Comparative Example 1-5 according to the General Elution Test, Japan Pharmacopeia, 14$^{th}$ Edition, paddle rotational speed: 50 revolutions per minute (using a sinker). Table 7 shows the resulting elution rate at this time.

Compared to the capsules of Comparative Example 1-5, the elution of the capsule preparations of Embodiment 1-10 and Embodiment 1-11 was faster.

TABLE 7

| Time | Embodiment 1-10 | Embodiment 1-11 | Comparative Example 1-5 |
|---|---|---|---|
| 15 minutes | 83.6% | 74.5% | 2.0% |
| 20 minutes | 87.0% | 86.6% | 13.1% |
| 30 minutes | 89.0% | 95.0% | 28.6% |

Test Example 2-1

The capsule preparations obtained in Embodiment 2-1 and Comparative Example 2-1 were placed into a glass desiccator which had a diameter of 15 cm with a depth of 15 cm and which contained a saturated aqueous solution of potassium nitric acid and they were stored there at 30° C. for a period of 2 days. The level of the relative humidity in the desiccator at this time was about 92%.

A metal disk with a diameter of about 6 mm was used to evaluate the presence or absence of cracks occurring after and before the storage when compression was applied with the pressure of 5 kg in the direction of the shorter diameter of the capsule and the ratio of the cracks was determined. In addition, the changes of external appearance after storage were also observed. Table 8 shows the results. While no damage was observed with any of the 10 capsules that were manufactured in Embodiment 2-1, damage occurred in all 10 capsules manufactured in Comparative Example 1-4 and it was also confirmed that the capsules were sticky.

TABLE 8

|  | Before the Storage | After the Storage | Changes of External Appearance after the Storage |
|---|---|---|---|
| Embodiment 2 - 1 | 0% | 0% | There were no changes in the external appearance compared to the status before the storage. |
| Comp. Example 2 - 1 | 0% | 100% | The capsule became sticky compared to the status before the storage. |

Test Example 2-2

The capsule preparations obtained in Embodiment 2-2 and Comparative Example 2-2 were placed into a glass desiccator which had a diameter of 15 cm with a depth of 15 cm and which contained a saturated aqueous solution of potassium nitric acid and they were stored there at 30° C. for a period of 8 days. The level of the relative humidity in the desiccator at this time was about 92%.

The capsule preparation was placed on a smooth glass plate that was free of irregularities and the plate was gradually tilted so that the angle at which the capsule preparation turned over and fell was measured before and after the storage. In addition, the changes in the external appearance after the storage were also observed. Table 9 shows the results.

TABLE 9

|  | Before the Storage | After the Storage | Changes of External Appearance after the Storage |
|---|---|---|---|
| Embodiment 2 - 2 | 6° | 5% | There were no changes in the external appearance compared to the status before the storage. |
| Comp. Example 2 - 2 | 6° | 57% | The capsule became sticky compared to the status before the storage. |

Test Example 3-1

Each of the 6 sugar-coated tablets obtained in Embodiment 3-1, Embodiment 3-2, Comparative Example 3-1 and Comparative Example 3-2 was tested in an elution test using the paddle method. A disk, which had a diameter of about 10 mm, a height of about 6 mm and a weight of 1.5 g was submerged in the center of the bottom part of a semi-cylindrical vessel using a separate vessel for each tablet so that 900 ml of water was used as a test solution to perform an elution test while the number of revolutions of the paddle was set to 50. Table 10 shows the coefficient of the fluctuations of the elution rate at this time.

The coefficient of the fluctuations of the elution rate in each time period indicated in the table is divided by the average elution rate during the desired time period determined for each of the 6 sugar-coated tablets. Therefore, it can be said the higher this value, the greater the extent of the fluctuations of elution. The sugar-coated tablets Embodiment 3-1 and Embodiment 3-2 had a smaller coefficient of fluctuations of the elution rate during this time period when compared to that of Comparative Example 3-1 and Comparative Example 3-2, and smaller fluctuations of elution were displayed by these sugar-coated tablets.

TABLE 10

| Time | Embodiment 3 - 1 | Embodiment 3 - 2 | Comp. Ex. 3 - 1 | Comp. Ex. 3 - 2 |
|---|---|---|---|---|
| 15 Minutes | 7.6% | 1.3% | 17.3% | 17.2% |
| 20 Minutes | 1.7% | 1.1% | 10.1% | 11.3% |
| 30 Minutes | 0.7% | 0.9% | 4.6% | 5.3% |

Test Example 3-2

Each of the 6 sugar-coated tablets obtained in Embodiment 3-1 and Embodiment 3-2 was tested in a general elution test according to the revised specification of the 14$^{th}$ Edition of Japan Pharmacopeia (Method 2) using 900 ml of water as the test solution, the number of the paddle revolutions was set to 50 revolutions and to 75 revolutions so that the elution test was carried out under 2 types of conditions. Table 11 shows the coefficient of the fluctuations of the elution rate during each time period. While a higher elution rate was determined for each tablet preparation when the number of the revolutions of the paddle was set to the usual speed of 50 revolutions during the test of the sugar-coated tablets obtained in Embodiment 3-1 and Embodiment 3-2, the rate of fluctuations determined when the number of the revolutions of the paddle was set to 75 rpm was smaller. Based on the test conditions, the results show that stabilized elution was obtained with the number of the paddle revolutions was set to 75 revolutions.

TABLE 11

Possibilities for Industrial Use

|  | Embodiment 3 - 1 | | Embodiment 3 - 2 | |
|---|---|---|---|---|
| Time | 50 Revolutions | 75 Revolutions | 50 Revolutions | 75 Revolutions |
| 15 Minutes | 18.0% | 7.3% | 25.0% | 6.4% |
| 20 Minutes | 10.2% | 3.8% | 20.1% | 3.6% |
| 30 Minutes | 5.0% | 1.8% | 14.5% | 1.4% |

The present invention provides a stabilized milnacipran formulation which has improved formulation deterioration characteristics when it is stored under high humidity conditions, as well as improved elution, which makes it possible to provide a stabilized pharmaceutical product.

The invention claimed is:

1. A composition comprising milnacipran used to manufacture a milnacipran formulation, wherein milnacipran or a salt thereof is adsorbed with a porous carrier containing anhydrous calcium hydrogen phosphate.

2. The composition described in claim 1, wherein the milnacipran or a salt thereof is milnacipran chloride.

3. The composition described in claim 1 or 2, wherein after the milnacipran or a salt thereof has been added to the porous carrier, the milnacipran or a salt thereof is adsorbed with the porous carrier, which is in a dried form.

4. A stabilized milnacipran formulation provided with improved tackiness, comprising the milnacipran composition described in claim 1.

5. A milnacipran formulation, comprising the milnacipran composition described in claim 1; wherein more than 80% of milnacipran or a salt thereof contained per the total amount of said formulation is present in the composition.

6. A milnacipran formulation comprising the milnacipran composition described in claim 1, wherein the milnacipran formulation is in the form of a sugar-coated tablet.

7. A milnacipran formulation comprising the milnacipran composition described in claim 1, which is loaded into a tablet.

8. A milnacipran formulation comprising the milnacipran composition described in claim 1, which is loaded into a capsule made of hydroxy propyl methyl cellulose (HPMC).

* * * * *